United States Patent [19]

Inary

[11] Patent Number: 5,777,161
[45] Date of Patent: Jul. 7, 1998

[54] PROCESS FOR PRODUCING HIGHLY PURE TEREPHTHALIC ACID BY USE OF DISPERSION MEDIUM REPLACEMENT APPARATUS

[75] Inventor: Masato Inary, Okayama-ken, Japan

[73] Assignees: Mitsubishi Gas Chemical Company, Inc., Tokyo; Toyo Boseki Kabushiki Kaisha, Osaka; Mizushima Aroma Company, Ltd., Kurashiki, all of Japan

[21] Appl. No.: 888,419

[22] Filed: Jul. 7, 1997

[30] Foreign Application Priority Data

Jul. 29, 1996 [JP] Japan .................................. 8-199142

[51] Int. Cl.$^6$ .................................................. C07C 51/42
[52] U.S. Cl. ............................................................. 562/485
[58] Field of Search ................................................ 562/485

[56] References Cited

U.S. PATENT DOCUMENTS 5,679,847 10/1997 Ohkoshi et al. .
5,684,187 11/1997 Ohkoshi et al. .
5,705,682 1/1998 Ohkoshi et al. .

*Primary Examiner*—Samuel Barts
*Attorney, Agent, or Firm*—Frishauf, Holtz, Goodman, Langer & Chick, P.C.

[57] ABSTRACT

There is disclosed a process for producing highly pure terephthalic acid by the use of a dispersion medium replacement apparatus equipped with a stirring unit at the bottom portion for uniform dispersion, wherein an original slurry comprising a first dispersion medium and terephthalic acid crystals is introduced into a dispersion medium replacement apparatus at the top portion, a second dispersion medium is introduced into the apparatus at the bottom portion, a replaced slurry comprising principally the second dispersion medium and the terephthalic acid crystals is taken out from the apparatus at the bottom portion, and the first dispersion medium as a major component is taken out from the apparatus at the top portion, which process comprises maintaining a uniformly dispersed slurry at the bottom portion of the apparatus at a concentration higher than that of a slurry at the intermediate portion; maintaining the upper portion at a higher temperature in a vertical temperature distribution therein to form a temperature change zone; and controlling the feed rate of the second dispersion medium and/or the takeout rate of the replaced slurry according to the location of the temperature change zone. By virtue of the specific control system, that is, taking advantage of the temperature change zone, the apparatus can be steadily operated with ease and high reliability at a high replacement efficiency, and thus highly pure terephthalic acid is stably obtained.

4 Claims, 2 Drawing Sheets

PROCESS FOR PRODUCING HIGHLY PURE TEREPHTHALIC ACID BY USE OF DISPERSION MEDIUM REPLACEMENT APPARATUS

BACKGROUND OF THE INVENTION

1. Field of the Invention

The present invention relates to a process for producing highly pure terephthalic acid by the use of a dispersion medium replacement apparatus. More particularly, it pertains to a process for producing highly pure terephthalic acid which comprises replacing, with another solvent for the purpose of purifying terephthalic acid, a dispersion medium in a slurry of crude terephthalic acid crystals which has been obtained by a liquid-phase oxidation reaction, or a dispersion medium in a slurry of terephthalic acid crystals which contains a considerable amount of impurities and which has been obtained by subjecting crude terephthalic acid to a catalytic hydrogenation treatment or a recrystallization treatment.

2. Description of the Related Arts

Terephthalic acid is produced by liquid-phase oxidation of a p-phenylene compound such as p-alkylbenzene typified by p-xylene. In this case, there are usually used acetic acid as a solvent and a catalyst such as cobalt and manganese incorporated as necessary, with a promotor exemplified by a bromine compound and acetaldehyde.

However, since the reaction uses acetic acid as a solvent and the reaction product contains such impurities as 4-carboxybenzaldehyde (4 CBA), p-toluic acid (p-TOL) and the like, considerably advanced purification technique is necessary in order to produce highly pure terephthalic acid.

As a method for purifying the crude terephthalic acid obtained by the liquid-phase oxidation reaction, mention is made of various known methods such as a method in which the crude terephthalic acid is dissolved in a solvent such as acetic acid, water or a mixed solvent thereof at a high temperature and high puresure and the resultant solution is subjected to a treatment by hydrogenation, decarbonization, oxidation or recrystallization and a method in which the crude terephthalic acid is subjected to an immersion treatment at a high temperature under a slurry condition in which terephthalic acid crystals are partially dissolved.

In any of the production process of crude terephthalic acid by liquid-phase oxidation reaction and the purification method thereof, there is finally required a procedure of separating terephthalic acid crystals from the dispersion medium.

However, the oxidation intermediate such as 4 CBA and p-TOL, and color causative substances that are present as impurities, in the oxidation reaction product or in the slurry formed by purification treatment of the crude terephthalic acid, are almost dissolved in the dispersion medium at a high temperature, but when any of the slurries is cooled to about 100° C. to form a slurry containing terephthalic acid crystal, these impuriteis are incorporated into the terephthalic acid crystal, thereby making it difficult to produce highly pure terephthalic acid.

Therefore, in order to separate highly pure terephthalic acid from the dispersion medium contained in the crude terephthalic acid slurry after the oxidation reaction or in the slurry formed after the purification treatment of the crude terephthalic acid, it is necessary to separate the terephthalic acid under the conditions of a high temperature and high pressure.

On the other hand, the most prevailing method for separating a dispersion medium from a slurry containing a crystal is centrifugal separation method, which is widely used also in the case of separating terephthalic acid crystals.

The centrifugal separation method is a method in which a slurry is introduced into a basket rotating at high speed to allow separated dispersion medium to overflow at the upside, and to direct separated crystals towards the underside. It is known, however, that a continuous operation of a centrifugal separator at a high temperature and pressure is accompanied by several difficulties arising from the restriction on the constitution and function of the centrifugal separator.

In the first place, crystal rinse is difficult during and after centrifugal separation and thus, the amount of dispersion medium stuck to the crystal is apt to increase. In order to eliminate the problem, a method in which the centrifugally separated terephthalic acid crystal in the form of cake is reslurried by means of fresh hot solvent is usually put into practice. However, the problem of necessitating separation procedure once more in this method still remains unsolved. Furthermore, the high-speed rotation at a high temperature and pressure results in troublesomeness and difficulty in the maintainance and preservation of the centrifugal separator, whereby the investment cost thereof is undesirably increased. In view of the foregoing, it can not be said that the centrifugal separation is a state-of-the-art technique in the field of solid/liquid separation.

There has recently been proposed a dispersion medium replacement apparatus which takes advantage of gravity settling of terephthalic acid crystals as a method taking the place of centrifugal separation method. For example, Japanese Patent Application Laid-Open Nos. 87744/1980 and 53431/1982 (EP 0321272) disclose a method in which a dispersion medium replacement apparatus is equipped inside with horizontal trays in order to enhance the replacement efficiency by avoiding channelling or back mixing of the fluid inside the apparatus. However, in the case of dealing with a slurry, especially in the case of using an apparatus taking advantage of gravity settling, the installation of such trays is accompanied by serious difficulties such as deposit or accumulation on the trays, clogging of openings, bulking, etc., thereby requiring much labor for stabilizing the operation. Thus, the installation of such trays is far from a state-of-the-art technique.

It has previously been found by the present inventors that the replacement of a dispersion medium is made possible simply with sufficient performance without the need of internal trays, by installing a stirring unit in the bottom portion of a dispersion medium replacement apparatus and further maintaining the slurry in the bottom portion of the apparatus at a concentration higher than that of the slurry in the intermediate portion of the apparatus, and thus a patent application was filed on the basis of the finding. (EP A 719576)

The above-mentioned apparatus, however, has four outlet/inlet ports including (1) a feed port for feeding an original slurry composed of a first dispersion medium and terephthalic acid crystals; (2) a feed port for introducing a second dispersion medium; (3) a discharge port for taking out a replaced slurry composed mainly of the terephthalic acid crystals and the second dispersion medium; and (4) a discharge port mainly for discharging the first dispersion medium. The feed rate or discharge rate other than the feed rate through the port (1) can optionally be varied, and such variation gives rise to operational flexibility and at the same

3 time, exerts significant influence on the performance such as the replacement efficiency for the dispersion medium. As a result, the flow rate management in the aforesaid system is considerably complicated, thereby making it difficult to stably and steadily operate the dispersion medium replacement apparatus.

SUMMARY OF THE INVENTION

Under such circumstances, intensive research and investigation were made on the dispersion medium replacement apparatus which in fact, has encountered such a serious difficulty as a commercial plant. As a result, it has been found that the dispersion medium replacement appparatus can be easily administrated by controlling the feed rate of the second dispersion medium and/or the takeout rate of the replaced slurry so as to maintain a temperature zone showing sharp change in temperature which can exist when the temperature distribution inside said apparatus is regulated so that the upper portion thereof is set to a higher temperature. The present invention has been accomplished by the aforestated finding.

Specifically the present invention provides a process for producing highly pure terephthalic acid by the use of a dispersion medium replacement apparatus equipped with a stirring unit at the bottom portion thereof for uniform dispersion therein, wherein an original slurry comprising a first dispersion medium and terephthalic acid crystals is introduced into a dispersion medium replacement apparatus at the top portion thereof, a second dispersion medium is introduced into said apparatus at the bottom portion thereof, a replaced slurry comprising principally the second dispersion medium and the terephthalic acid crystals is taken out from said apparatus at the bottom portion thereof, and the first dispersion medium as a major component is taken out from said apparatus at the top portion thereof, which process comprises maintaining a uniformly dispersed slurry at the bottom portion of the apparatus at a concentration higher than that of a slurry at the intermediate portion thereof; maintaining the upper portion thereof at a higher temperature in a vertical temperature distribution therein to form a temperature change zone; and controlling at least one of the feed rate of the second dispersion medium and the takeout rate of the replaced slurry in accordance with the location of said temperature change zone.

BRIEF DESCRIPTION OF THE DRAWINGES

FIG. 1 is a drawing showing an example of a block flow diagram of a process for producing highly pure terephthalic acid and a flow diagram of a dispersion medium replacement apparatus in the present invention; and FIG. 2 is a drawing showing a result of a measurement of a temperature distribution inside a dispersion medium replacement apparatus in Example 1.

DESCRIPTION OF THE PREFERRED EMBODIMENTS

Figure 1:
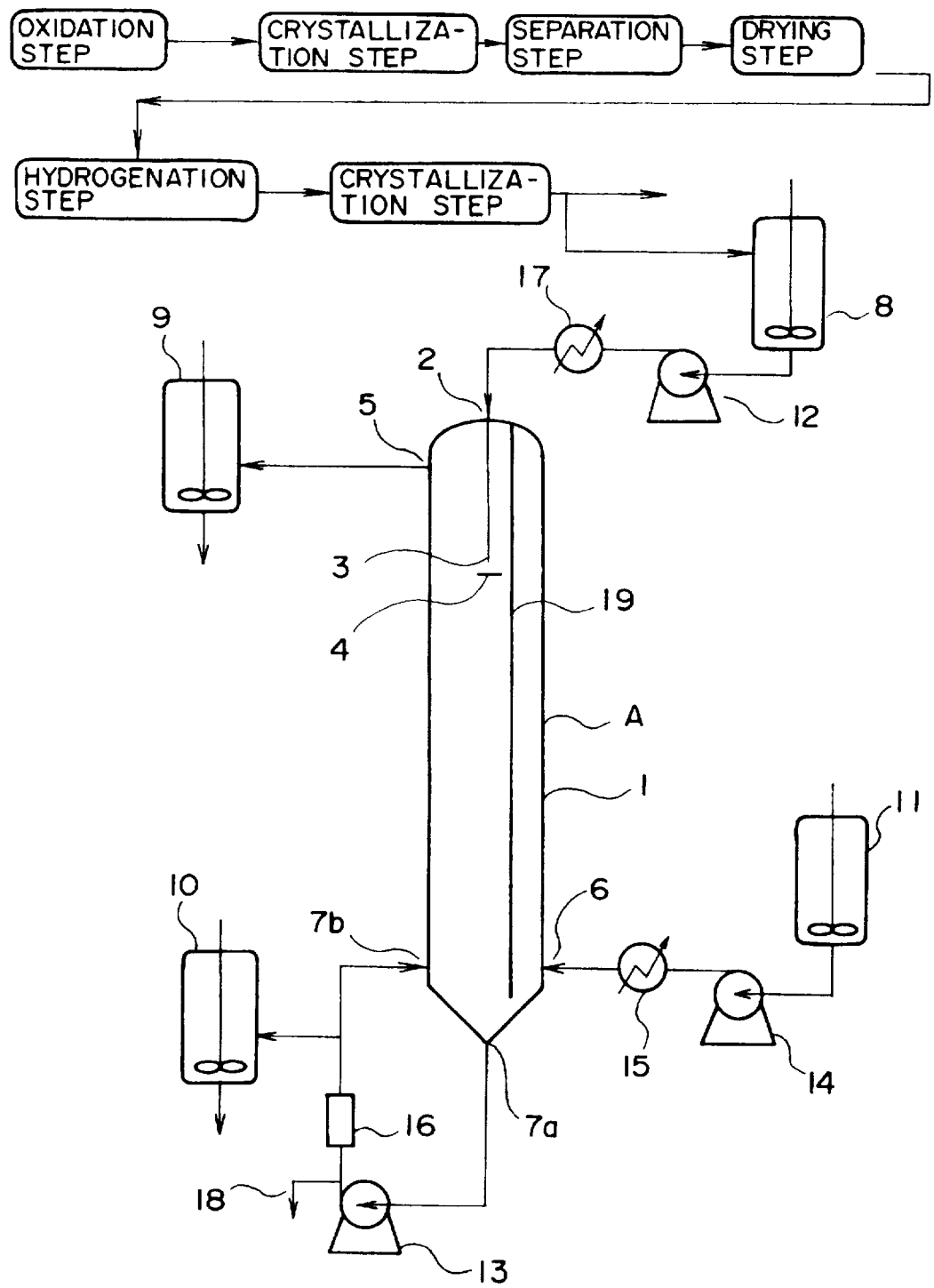

The dispersion medium replacement apparatus according to the present invention is employed for the treatment of a slurry of crude terephthalic acid crystals which has been obtained by a liquid-phase oxidation reaction, or a slurry of terephthalic acid crystals which contains a considerable amount of impurities and which has been obtained by subjecting crude terephalic acid to a catalytic hydrogenation treatment or a recrystallication treatment.

In general, acetic acid as a solvent is frequently used in a liquid-phase reaction, while water as a solvent is frequently used in a catalytic hydrogenation treatment. In the case where the slurry of crude terephthalic acid crystals is subjected to a solvent replacement treatment in a dispersion medium replacement apparatus in such cases, a first and a second dispersion media are acetic acid and water, respectively.

The above-mentioned apparatus according to the present invention is usable also for purifying a slurry of terephthalic acid crystals, and in the case, for example, of purifying treating a slurry of terephthalic acid crystals obtained by the above-mentioned catalytic hydrogenation treatment, the first and second dispersion media are each water.

The first dispersion medium, that is, the dispersion medium to be replaced may be the same as or different from the second dispersion medium, that is, the replacing medium.

The dispersion medium replacement apparatus according to the present invention need not internal trays in particular, and is usually in the form of empty tower. The stirring unit to be placed at the bottom portion of the apparatus needs only to be capable of substantially uniformly dispersing the slurry at the bottom portion thereof. Examples of the usable stirring unit include so called a stirrer equipped with various agitation impellers and a circulation pump which causes mixed flow at the bottom portion thereof. In addition, it is preferably carried out to install baffle plates to promote stirring. In this case, the concentration of the slurry at the bottom portion thereof can be kept at a high level by controlling the feed rate of the dispersion medium to be fed at the bottom portion as well as the takeout rate of the replaced slurry.

It is particularly preferable that a slight upward stream be generated in the apparatus in order to maintain a high replacement efficiency in the apparatus. In the event of a downward stream being generated in the apparatus, a part of the first dispersion medium to be discharged at the port (4) is sometimes mixed in the stream towards the discharge port (3) of the replaced slurry, which is an unfavorable factor of impairing the object of replacing the first dispersion medium with the second dispersion medium. Accordingly, such a downward stream should be prevented by al means. It is also known that the performance of the apparatus greatly depends upon the intensity of the upward stream.

However, with regard to the stream in the dispersion medium replacement apparatus, for example, the stream is the difference between the feed rate of the second dispersion medium (2) and the takeout rate of the liquid components in the replaced slurry (3), and thus the stream can not be regulated as an independent flow rate. To further troblesomeness, it is necessary to recognize on time, the solid concentration in the replaced slurry in order to recognize the flow rate of the liquid components in the replaced slurry. The solid concentration is a physical quantity involving much errors among all physical quantities to be detected whereby it is extremely difficult to detect the same on time Even though the solid concentration is not undetectable provided that considerable variations are accepted with resignation, the upward flow rate to be administrated in the apparatus is a slight flow rate about one tenth the main flow rate which is the basis of the difference, and therefore some accuracy of the detected solid concentration is required in response to the aforesaid slight flow rate.

The administration of the flow rate is, of course, made easy by increasing the upward flow rate. However, when the upward flow rate is increased, it consequently follows that the amount of the first dispersion medium discharged at (4 is increased. The first dispersion medium is finally discharged outside the system as an effluent. Accordingly, from the aspect of minimizing the amount of the effluent, the upward flow rate must be restricted without any choice.

It has been confirmed according to the process of the present invention that a zone showing a characteristic temperature distribution, that is, an extremely sharp temperature change in the vertical direction is formed, by maintaining the temperature at the upper portion of the apparatus at a relatively high level as compared with that at the lower portion, and at the same time, maintaining the slurry concentration at the bottom portion at a relatively high level as compared with that at the intermediate portion.

In the case where an empty column is filled in with a fluid and temperature difference is caused between the upper portion and the lower portion with a slight stream of the fluid, it is common knowledge that there is shown a temperature distribution having a gentle gradient from the upper portion to the lower portion. Nevertheless, such a sharp temperature change as mentioned above is indeed nothing but a fact overturining the common knowledge.

As a result of investigation on the zone showing sharp change in temperature, it has been elucidated that the posistion of the zone showing sharp change in temperature is highly responsive to the upward stream inside the apparatus and at the same time, it has been understood that the upward stream can be controlled by controlling the location of such zone.

The position of the zone is elevated with increase in the upward stream, and is lowered with decrease in the upward stream. Accordingly, the detection of the lowered zone means a decrease in the upward stream. In such a case, the upward stream is intensified to maintain high replacement efficiency in the dispersion medium replacement apparatus by carrying out a procedure of intensifying the upward stream, for example, a procedure of increasing the feed rate of the second dispersion medium, or decreasing the takeout rate of the replaced slurry.

The procedure of causing tremperature difference between the upper portion and the lower portion, that is, operating the vertical temperature distribution so as to maintain the upper portion at a higher temperature can be put into practice, for example, by setting the temperature of the second dispersion medium to a temperature lower than that of the feed slurry. The adoption of the aforesaid operational method enables not only the replacement efficiency in the apparatus to be maintained at a high level, but also the operational system to be more steadily constituted by the specific gravity of the dispersion medium in the slurry at the bottom portion being made higher than that of the dispersion medium in the feed slurry.

The dispersion medium replacement apparatus can easily be operated under pressure because of its simplified structure and closed system, and is preferably used at a temperature not higher than the boiling point of each of the dispersion media at the operational pressure.

The dispersion medium replacement apparatus, which has two feed ports and two discharge ports, has heretofore made it considerably troublesome to administrate the flow rate through each of the feed ports and discharge ports. However, the process according to the present invention can facilitate the administration of the apparatus and steadily maintain a high replacement efficiency.

As described hereinbefore, it is made possible to steadily operate in a high replacement efficiency with ease, the dispersion medium replacement apparatus in which a feed port of a slurry requiring dispersion medium replacement is installed at the top portion thereof, a desired dispersion medium feed portion is formed at the bottom portion thereof, said dispersion medium feed portion is brought into a uniform dispersion state and the concentration of the slurry at the bottom portion is made higher than that of the slurry inside a cylindrical column, by maintaining the upper portion thereof at a higher temperature in the vertical temperature distribution in the apparatus; detecting the vertical temperature distribution therein at each operation time; and controlling the feed rate of the second dispersion medium or the takeout rate of the replaced slurry in accordance with the position of the zone showing a sharp change in temperature.

The process according to the present invention, which is a process carrying out the operational control by means of the zone showing a change in temperature, can easily readily be put into operation and can assure high reliability, thereby rendering itself extremely excellent from the industrial aspect.

By operating the dispersion medium replacement apparatus by the use of the process according to the present invention, it is made possible to steadily carry out dispersion medium replacement as well as purification of a slurry of terephthalic acid in the process for producing terephthalic acid without the use of a centrifugal separator or the like. Thus a highly advantageous process for producing terephthalic acid is established.

In the following, the present invention will be described in more detail with reference to a comparative example and a working example, which however, shall not limit the present invention therto.

EXAMPLE 1

In FIG. 1 illustrating the block flow diagram of the process for producing highly pure terephthalic acid which was used in Example 1, p-xylene or the like is subjected to a liquid-phase oxidation reaction by usually using acetic acid solvent in the oxidation step; in the crystallization step, crude terephthalic acid is precipitated by cooling; in the separation step, the resultant crude terephthalic acid is subjected to crystal separation usually with a centrifugal separator; in the drying step, the separated crystals are dried; in the hydrogenation step, the crude terephthalic acid is purified by catalytic hydrogenation reaction in the presence of a water solvent to form refined terephthalic acid; and in the next crystallization step, a slurry of the refined terephthalic acid is produced.

FIG. 1 further illustrates a flow diagram of a dispersion medium replacement apparatus where the slurry of refined terephthalic acid produced in the aforesaid crystallization step is treated in a dispersion medium replacement column A.

The dispersion medium replacement apparatus comprises a dispersion medium replacement column A as the main element, an original slurry tank 8, a replacing dispersion medium tank 11 for feeding a second dispersion medium, an overflow dispersion medium tank 9 for receiving replaced first dispersion medium, a replaced slurry tank 10 for receiving the discharged replaced slurry, each of the tanks being connected to the column A and necessary liquid feed and stirring pumps 12, 13 and 14.

The dispersion medium replacement column A is a stainless steel-made cylindrical column having 100 $^{mm}$ inside diameter and vertically long structure.

Into the top portion of the apparatus is introduced the original slurry through an introduction system comprising a slurry receiving port 2 which is connected to the original slurry tank 8 and an introduction port for the original slurry 3 that extends to the upper portion of the column is equipped with a dispersion plate 4 assisting slurry dispersion at the end thereof. The original slurry comprising the first dispersion medium and terephthalic acid crystals is transferred from the original slurry tank 8 to the slurry receiving port 2 via an original slurry transfer pump 12, and is sprinkled inside the upper portion of the column.

Most of crystalline particles of terephthalic acid, in the original slurry thus sprinkled, settle in the cylindrical column 1. Particularly fine particles which form a part of the crystalline particles and the first dispersion medium overflow in an overflow dispersion medium tank 9 from the first dispersion medium overflow part 5 at the upper part of the side of the replacement column.

To the lower end of the column is connected a stirring pump 13, which stirs the internal fluid in the bottom portion of the column through the circulating flow which starts from a replaced slurry takeout unit 7a and reaches a recycle return port 7b via the pumb 13. The replaced slurry is taken out through a line branched from a discharge line of the pump 13, and the replaced slurry thus taken out is stored in a replaced slurry tank 10. A replacing second dispersion medium is fed in the column 1 at a replacing dispersion medium feed port 6 at the lower part of the side of the column 1 from a replacing dispersion medium tank 11 via a replacing dispersion medium tranfer pump 14.

A sheath tube for temperature measurement 19 was installed in the column A to insert thermometers from the top to the bottom thereof, and a measurement was made in detail of the temperature distribution in the vertical direction of the column A.

By the use of above-described apparatus, the dispersion medium in a slurry of terephthalic acid crystals was replaced with fresh water, said slurry being produced by purifying, through catalytic hydrogenation and recrystallization in the presence of a water solvent, crude terephthalic acid which had been produced by air-oxidizing p-xylene at a reaction temperature of 200° C. and a pressure of 16 atm. in the presence of manganese acetate, cobalt acetate and hydrobromic acid as oxidation catalysts in a water-containing acetic acid as a solvent by the use of a commercial scale apparatus, followed by crystallization, separation and drying of the terephthalic acid.

The resultant crude terephthalic acid was dissolved in hot water, the resulting aqueous solution was passed through a packed bed of palladium catalyst supported on activated carbon to subject impurities to a catalytic hydrogenation treatment at 280° C. in the presence of hydrogen and thereafter was introduced in crystallization tanks that were connected to one another in series to consecutively depressurize and cool down to 100° C. so as to collect refined slurry of terephthalic acid crystals. The slurry thus collected was fed to the original slurry tank 8 as the original slurry.

First of all, the refined terephthalic acid crystals were fed in the bottom portion of the column, in which was fed fresh water while it was heated to 100° C. by passing through a heat exchanger 15 with the pump 14, and stirring was installed by actuating the pump 13 to disperse the crystals to attain a crystal concentration of 30% by weight. When the fluid level in the column 1 reached the port 5, the pump 12 was actuated to start original slurry feeding and at the same time, taking out of the replaced slurry into the tank 10 was started. The original slurry as the starting material was heated to 150° C. through a heat exchanger 17 on the way to the column 1.

The slurry concentration at the bottom portion of the column was obtained by converting the density which had been detected with an on-line density meter 16, while it was obtained by sampling the slurry at hourly intervals at a sampling port 18 on the delivery line of the stirring pump 13, and separating and drying the slurry to calculate its concentration.

The feed rates and discharge rates were as follows:

| | |
|---|---|
| Feed rate of the original slurry | 40.5 kg/hr |
| Feed rate of the second dispersion medium | 31.7 kg/hr |
| Discharge rate of the overflow dispersion medium | 38.0 kg/hr |
| Discharge rate of the replaced slurry | 37.7 kg/hr |

The operation conditions were set so as to achieve a feed slurry concentration of 30%, a takeout slurry concentration of 32% and an upward linear velocity of 0.76 m/hr, which was obtained by dividing the upward flow rate by the cross-section area inside the apparatus.

Figure 2:
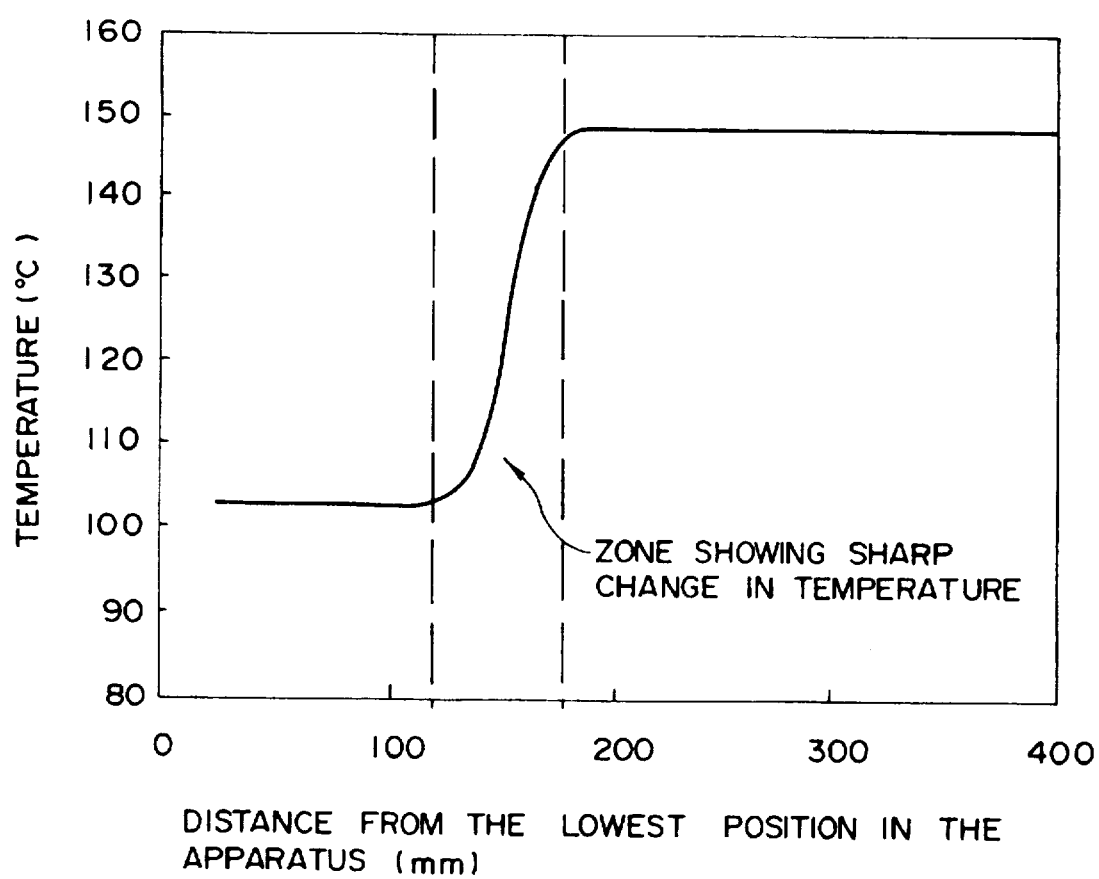

After 30 minutes from the start of the experiment, there was distinctly observed as given in FIG. 2, a portion showing sharp change in temperature in the vertial direction in the column A, ranging from a distance of 120 mm from the lowest portion in the apparatus to the distance of 170 mm therefrom. Thereafter, the aforesaid zone was regulated to a definite position by increasing the flow rate of the second dispersion medium from the replacing dispersion medium feed port 6 when said portion was descending, and decreasing the same when it was ascending.

After several hours of continuous operation, the stream of fluid in the system reached a sufficiently steady state, and then analysis was made of the concentration of benzoic acid in the dispersion medium in the slurry introduced into the column and of the same in the dispersion medium in the liquid inside the replaced slurry tank 10.

The replacement efficiency in the dispersion medium replacement apparatus is defined as the ratio of the amount of benzoic acid contained in the overflowing dispersion medium which has been replaced and overflowed through the port 5, to the amount of the benzoic acid in the dispersion medium in the original slulrry, that is, the percentage of the amount of the benzoic acid which has been separated through replacement from the main stream containing a large amount of terephthalic acid.

In Table 1 is given the result of a measurement of the change in the foregoing replacement efficiency with the lapse of time on the basis of sampling at hourly intervals.

TABLE 1

| Lapse of time (Hr) | Replacement efficiency (%) |
|---|---|
| 3 | 92.2 |
| 4 | 92.0 |
| 5 | 92.0 |
| 6 | 92.3 |
| 7 | 91.8 |
| 8 | 92.2 |
| 9 | 92.3 |
| 10 | 92.0 |

It can be seen from Table 1, that the replacement efficiency is remarkably stable and that a stable replacemen efficiency can be maintained by a properly administrating method for an upward linear velocity which comprises measuring the temperature distribution in the vertical direction in the dispersion medium replacement column A and regulating the flow rate of the second dispersion medium so that the zone showing sharp change in temperature is located at a same position at all times.

COMPARATIVE EXAMPLE 1

The apparatus same as in Example 1 was operated under the same conditions for each flow rate as in Example 1, but the concentration of the replaced slurry was calculated from the density thereof detected with the on-line density meter 16, the flow rate of the dispersion medium was presumed from the flow rate and the calculated concentration of the replaced slurry, and the administration of the upward linear velocity was carried out on the basis of the upward linear velocity obtained from the difference between the flow rate of the second dispersion medium and the above-presumed florw rate of the dispersion medium. The rusluts are given in Table 2.

TABLE 2

| Lapse of time (Hr) | Replacement efficiency (%) |
|---|---|
| 3 | 91.2 |
| 4 | 88.9 |
| 5 | 93.0 |
| 6 | 92.3 |
| 7 | 90.5 |
| 8 | 90.1 |
| 9 | 93.1 |
| 10 | 89.2 |

As is clear from Table 2, the variation in the replacement efficiency was markedly great, since the density detected with the on-line density meter involves an error of several %, which is amplified to the error of the difference between the flow rate of the second dispersion medium and the above-presumed flow rate of the dispersion medium.

What is claimed is:

1. A process for producing highly pure terephthalic acid by the use of a dispersion medium replacement appartus equipped with a stirring unit at the bottom portion thereof for uniform dispersion therein, wherein an original slurry comprising a first dispersion medium and terephthalic acid crystals is introduced into a dispersion medium replacement apparatus at the top portion thereof, a second dispersion medium is introduced into said apparatus at the bottom portion thereof, a replaced slurry comprising principally the second dispersion medium and the terephthalic acid crystals is taken out from said apparatus at the bottom portion thereof, and the first dispersion medium as a major component is taken out from said apparatus at the upper portion thereof, which process comprises maintaining a uniformly dispersed slurry at the bottom portion of the apparatus at a concentration higher than that of a slurry at the intermediate portion thereof; maintaining the top portion thereof at a higher temperature in a vertical temperature distribution therein to form a temperature change zone; and controlling at least one of the feed rate of the second dispersion medium and the takeout rate of the replaced slurry in accordance with the location of said temperature change zone.

2. The process according to calim 1 wherein a slight upward-stream is generated in the apparatus.

3. The process according to calim 1 wherein the second dispersion medium is maintained at a temperature lower than that of the original feed slurry.

4. The process according to claim 1 wherein the first dispersion medium is water or acetic acid, and the second dispersion medium is water.

* * * * *